United States Patent [19]

Kodama et al.

[11] Patent Number: 5,629,332

[45] Date of Patent: May 13, 1997

[54] TRIAZOLE COMPOUND AND USE THEREOF

[75] Inventors: Hiroki Kodama; Michihiko Kawaguchi; Yoshiyuki Kato; Yoshimi Niwano, all of Osaka; Masanori Yoshida, Wakayama, all of Japan

[73] Assignee: Nihon Nohyaku Co., Ltd., Tokyo, Japan

[21] Appl. No.: 411,210

[22] Filed: Mar. 27, 1995

[30] Foreign Application Priority Data

Mar. 28, 1994 [JP] Japan ................................. 6-080889

[51] Int. Cl.$^6$ .................. A61K 31/41; C07D 249/08
[52] U.S. Cl. .................. 514/383; 548/266.6; 548/263.2; 548/268.4; 548/268.6; 546/272.4; 514/340
[58] Field of Search .................. 548/268.4, 268.6, 548/266.6, 263.2; 514/383

[56] References Cited

U.S. PATENT DOCUMENTS

| | | | |
|---|---|---|---|
| 4,505,919 | 3/1985 | Cooper et al. | 514/340 |
| 4,584,308 | 4/1986 | Elbe et al. | 514/383 |
| 4,879,385 | 11/1989 | Elbe et al. | 514/383 |
| 5,116,844 | 5/1992 | Dickinson et al. | 514/383 |

FOREIGN PATENT DOCUMENTS

| | | |
|---|---|---|
| 0111234 | 6/1984 | European Pat. Off. . |
| 0150036 | 7/1985 | European Pat. Off. . |
| 0332387 | 9/1989 | European Pat. Off. . |
| 0613890 | 9/1994 | European Pat. Off. . |
| 1275566 | 6/1989 | Japan . |

OTHER PUBLICATIONS

CA 108:6023, Schaper et al. 1988.
Derwent Patent Abstract, JP-01275566, 1995.

*Primary Examiner*—Jane Fan
*Attorney, Agent, or Firm*—Sughrue, Mion, Zinn, Macpeak & Seas

[57] ABSTRACT

A triazole compound or a pharmacologically acceptable salt thereof represented by the following formula (I)

wherein $R_1$ and $R_2$ are the same or different from each other and each represents a hydrogen atom, a halogen atom or a $C_1$–$C_6$ trihaloalkyl group, $R_3$ represents a phenyl group which may be substituted or a heterocyclic aromatic ring which may be substituted and X represents S, $SO_2$ or —$(CH_2)_n$— where n is 0 or an integer of 1 to 2, excluding a case in which $R_1$ and $R_2$ are hydrogen atoms at the same time.

3 Claims, No Drawings

TRIAZOLE COMPOUND AND USE THEREOF

FIELD OF THE INVENTION

This invention relates to an antifungal agent which contains a novel triazole compound or a pharmaceutically acceptable salt thereof as an active ingredient.

BACKGROUND OF THE INVENTION

Since the introduction of several triazole drugs such as ketoconazole, fluconazole and itraconazole, antimycotic chemotherapy has extremely progressed. But recently, it is recognized that their therapeutic efficacy are not always satisfied.

Though EP-333059A discloses that a compound having a structure similar to that of the triazole compound of the present invention is possessed of an agriculturally useful germicidal activity, there is no description on its medically useful antifungal activity.

In particular, decrease in the immunological competence caused by immunodeficiency or by the use of anticancer drugs and the like has been posing a problem of inducing fungous diseases due to fungal infection.

Therefore, new antimycotic agents having superior activity against fungal infection are still expected.

SUMMARY OF THE INVENTION

In view of the above, the inventors of the present invention have conducted intensive studies with the aim of providing an antifungal agent and found as the result that a compound represented by the following formula (I) can show an antifungal activity with a low dose.

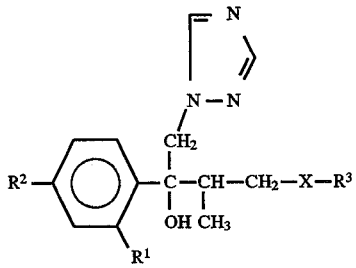

In the above formula, $R_1$ and $R_2$ are the same or different from each other and each represents a hydrogen atom, a halogen atom or a $C_1$–$C_6$ trihaloalkyl group, $R_3$ represents a phenyl group which may be substituted or a heterocyclic aromatic ring which may be substituted and X represents S, $SO_2$ or —$(CH_2)_n$— where n is 0 or an integer of 1 to 2, excluding a case in which $R_1$ and $R_2$ are hydrogen atoms at the same time. The present invention has been accomplished on the basis of the above finding.

DETAILED DESCRIPTION OF THE INVENTION

With regard to the definition of substituent groups of the aforementioned formula (I), illustrative examples of the halogen atom include fluorine, bromine, chlorine and the like atoms, those of the trihaloalkyl group include trifluoromethyl, trichloromethyl and the like groups. Illustrative examples of the heterocyclic aromatic ring include 1,2,4-triazolyl, thiazolyl, isothiazolyl, thienyl, furyl, pyridyl, imidazolyl, pyrazinyl, oxazolyl, isoxazolyl, thiazolyl, thiadiazolyl, pyrazolyl, imidazopyrimidyl, benzothiazolyl, benzimidazolyl and the like groups. The phenyl group and the heterocyclic aromatic ring may be substituted, and illustrative examples of such substituent groups include halogen atoms such as fluorine, bromine, chlorine and the like atoms, $C_1$–$C_6$ alkyl groups such as methyl, ethyl, n-propyl, isopropyl, n-butyl, isobutyl, sec-butyl, tert-butyl, n-pentyl, 1-methylbutyl, 2-methylbutyl, 1,2-dimethylpropyl, n-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like groups, $C_1$–$C_6$ alkoxy groups such as methoxy, ethoxy, n-propoxy, isopropoxy, n-butoxy, isobutoxy, sec-butoxy, tert-butoxy, n-pentoxy, n-hexyloxy and the like groups, $C_1$–$C_6$ alkylthio groups such as methylthio, ethylthio, n-propylthio, isopropylthio, n-butylthio, isobutylthio, sec-butylthio, tert-butylthio and the like groups, $C_1$–$C_6$ alkylsulfonyl groups such as methylsulfonyl, ethylsulfonyl and the like groups, $C_1$–$C_6$ haloalkyl groups such as fluoromethyl, chloromethyl, bromomethyl, difluoromethyl, dichloromethyl, dibromomethyl, trichloromethyl, trifluoromethyl, 2-fluoroethyl, 2-chloroethyl, 2-bromoethyl, 1,1,1-trifluoroethyl, 2,2,2-trifluoroethyl and the like groups, $C_1$–$C_6$ haloalkoxy groups such as 1-chloroethoxy, 1-bromoethoxy, 3-bromo-n-propoxy, difluoromethoxy, 1,1,1-trifluoroethoxy, 1,1,2-trifluoroethoxy and the like groups, $C_1$–$C_6$ haloalkylthio groups such as 2-chloroethylthio, 2-bromoethylthio, 3-bromo-n-propylthio, 1,1,1-trifluoroethylthio, difluoromethylthio, 2,2,2-trifluoroethylthio and the like groups, cyano group, amino group, nitro group, imino group, formyl group, formylhydrazonylmethyl group and aromatic heterocyclic groups.

The compound of the present invention, wherein $R_1$ and $R_2$ are the same or different from each other and each represents a halogen atom or a $C_1$–$C_4$ trihaloalkyl group, $R_3$ is a pheny group substituted with 1 or 2 substituting groups selected from halogen atoms, $C_1$–$C_4$ haloalkoxy groups, $C_1$–$C_4$ alkylthio groups, $C_1$–$C_4$ haloalkylthio groups, nitro group, cyano group and 1,2,4-triazolyl group and X is a single bond or a $C_1$–$C_2$ alkylene group is more preferable.

Two diastereomers are present in the compound represented by the formula (I), and they can be separated by a known method such as a silica gel column chromatography, a high performance liquid chromatography or the like. In addition, each of the diastereomers can be separated as its corresponding enantiomer by a known method such as an optically active resolution column technique or the like. In consequence, separated or mixed form of these diastereomers and enantiomers are included in the compound of the present invention represented by the formula (I).

The compound (I) of the present invention can be used as an antifungal agent as it is or in the form of an acid addition salt. Illustrative examples of the acid to be used include inorganic acids such as hydrochloric acid, sulfuric acid, nitric acid and the like and organic acids such as oxalic acid, methanesulfonic acid and the like.

The compound (I) of the present invention can be synthesized for example by the following methods.

Method A

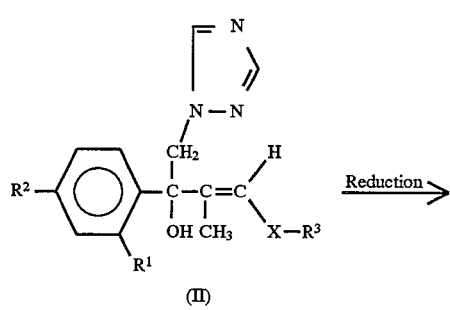

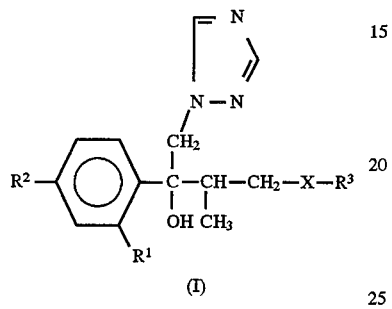

In this reaction formula, $R_1$, $R_2$, $R_3$ and X are as defined in the foregoing.

That is, the compound represented by the formula (I) can be obtained by subjecting a compound represented by a formula (II) to hydrogenation in the presence of a metal catalyst or to reduction using a hydrogenation agent. As the metal catalyst, palladium, rhodium, platinum or the like single metal can be used. Each of these metals may also be used by supporting it on a carrier such as carbon, alumina or the like. In the practice of this reaction, the metal catalyst may be used generally in a catalytically effective amount or, if necessary, in an equivalent or excess amount.

Any solvent which does not inhibit progress of this reaction can be used in the reaction, such as methanol, ethanol, acetonitrile, dimethylformamide, acetic acid, dimethyl sulfoxide, tetrahydrofuran, water or a mixture thereof.

The reaction temperature may be selected optionally from the range of from −20° C. to the boiling point of each solvent. Though the reaction time varies depending on the reaction temperature and reaction scale, it may be selected optionally from the range of from 0.5 to 48 hours.

After completion of the reaction, the compound of interest is purified in the usual way, and its enantiomers are separated making use of a conventional means such as an optical isomer separation column or the like.

As an alternative reduction method, the reduction can be effected by the use of an appropriate hydrogenation agent. As the hydrogenation agent, lithium aluminium hydride, borane, aluminium hydride, diisobutylaluminium hydride or the like can be used. In the practice of this reaction, the hydrogenation agent may be used in an equivalent molar ratio or in an excess amount as occasion demands. Any solvent which does not inhibit progress of this reaction can be used in the reaction, such as methanol, ethanol, diethyl ether, methylene chloride, tetrahydrofuran or a mixture thereof. The reaction temperature may be selected optionally from the range of from −80° C. to the boiling point of each solvent. Though the reaction time varies depending on the reaction temperature and reaction scale, it may be selected optionally from the range of from 0.5 to 48 hours.

The compound represented by the formula (II) can be synthesized in accordance with the procedure disclosed in EP-333059A and EP-613890A.

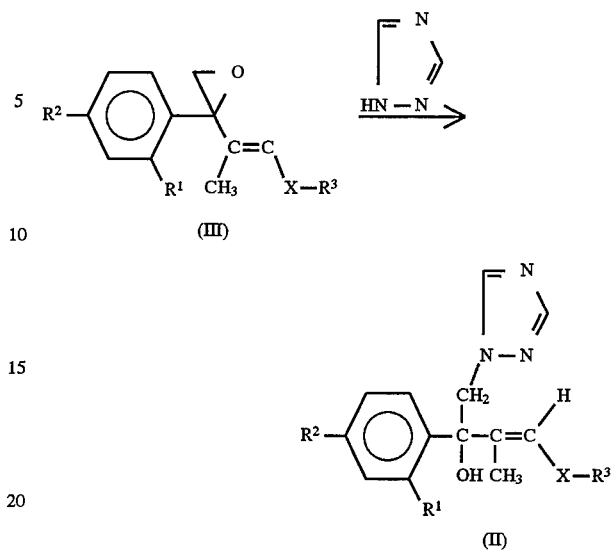

In this reaction formula, $R^1$, $R^2$, $R^3$ and X are as defined in the foregoing.

Method B

The compound represented by the formula (I) can be obtained by allowing a compound represented by a formula (IV) to react with 1,2,4-triazole in an inert solvent in the presence of a base.

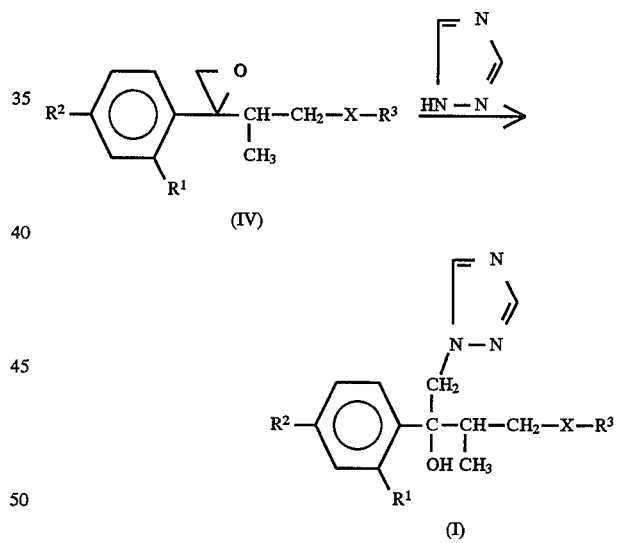

In this reaction formula, $R^1$, $R^2$, $R^3$ and X are as defined in the foregoing.

In the practice of this reaction, the reactants may be used in an equivalent molar ratio or one of them may be used in an excess amount.

Any solvent which does not inhibit progress of this reaction can be used in the reaction, such as methanol, ethanol, acetonitrile, dimethylformamide, dimethyl sulfoxide, tetrahydrofuran, acetic acid, water or a mixture thereof.

The reaction temperature may be selected optionally from the range of from −20° C. to the boiling point of each solvent. Though the reaction time varies depending on the reaction temperature and reaction scale, it may be selected optionally from the range of from 0.5 to 48 hours.

The compound represented by the formula (IV) can be synthesized from a compound represented by a formula (VI) in accordance with a known method such as a method reported in *J. Am. Chem. Soc.*, 84, 867 (1962) or in *Pesticide Science*, 31, 457 (1991).

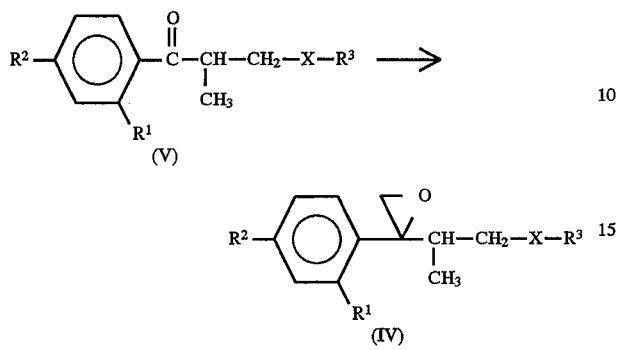

In this reaction formula, $R^1$, $R^2$, $R^3$ and X are as defined in the foregoing.

The compound represented by the formula (V) can be synthesized generally by the following methods.

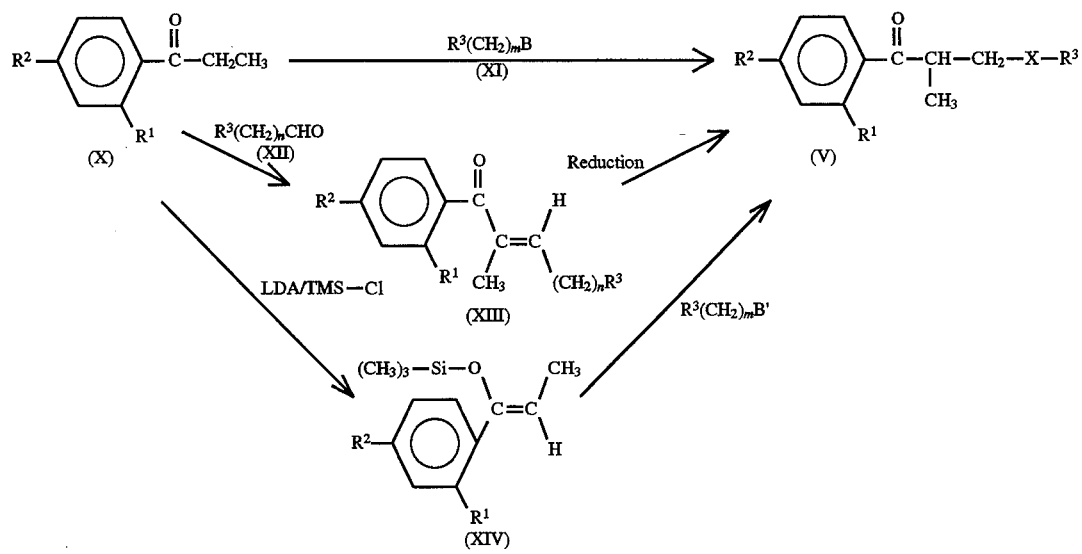

Method A

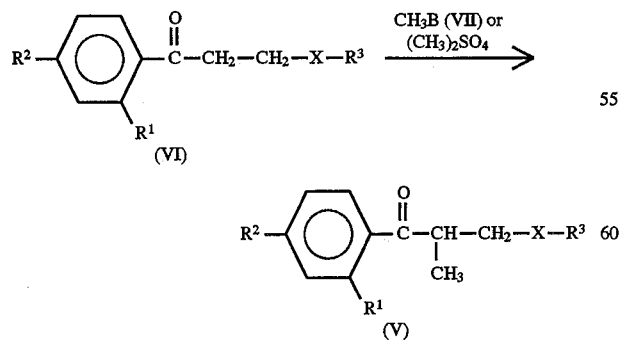

In this reaction formula, $R^1$, $R^2$, $R^3$ and X are as defined in the foregoing and B is a halogen atom.

That is, it can be synthesized by subjecting the compound represented by the formula (VI) to methylation with an appropriate methylation agent.

Method B

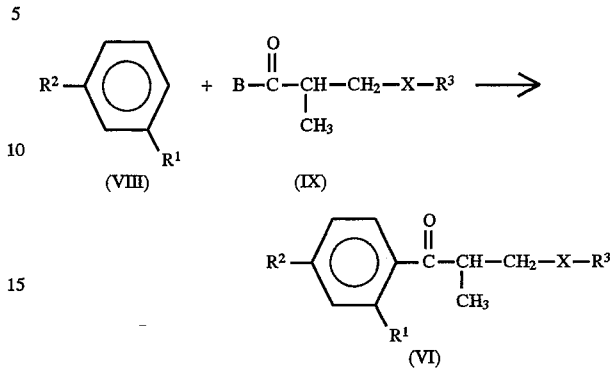

In this reaction formula, $R^1$, $R^2$, $R^3$, B and X are as defined in the foregoing.

That is, it can be obtained by Friedel-Crafts' reaction of a benzene derivative represented by the formula (VIII) with a compound represented by the formula (IX).

Method C (When X is —$(CH_2)_n$—)

In this reaction formula, $R^1$, $R^2$, $R^3$ and X are as defined in the foregoing, B' represents a chlorine, bromine or the like halogen atom, a p-toluenesulfonyloxy group or a methane-sulfonyloxy group, n is an integer of 1 or 2 and m is an integer of 1 to 3.

That is, it can be obtained by reduction after alkylation or aldol condensation from a propiophenone (X).

Method D (When X is —S— or —SO$_2$—)

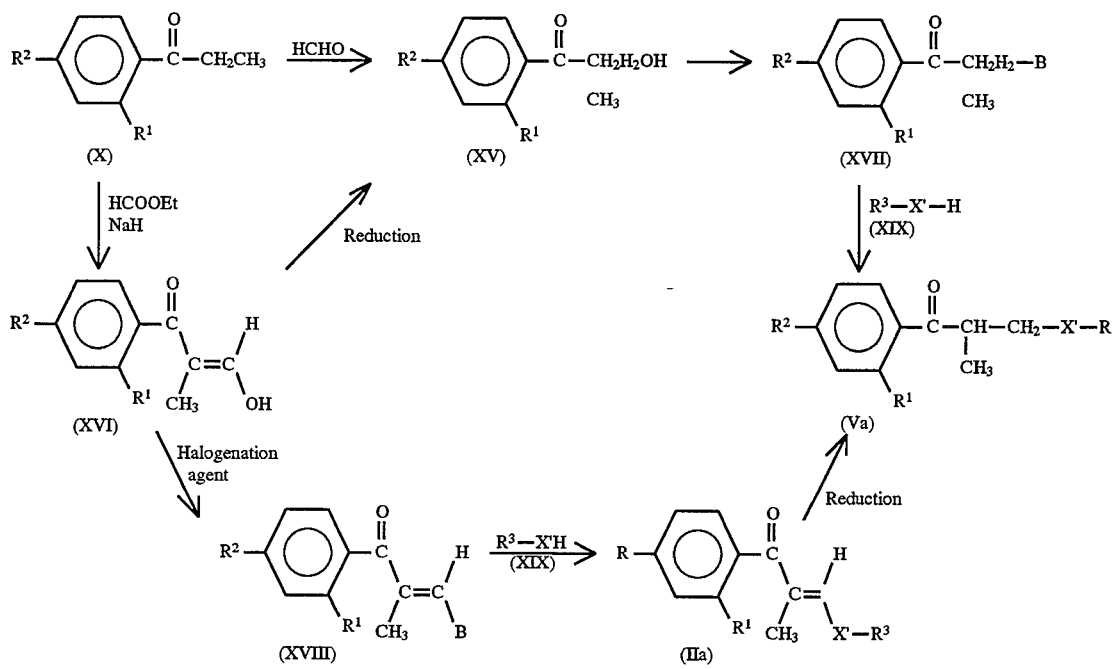

In this reaction formula, $R^1$, $R^2$, $R^3$ and X are as defined in the foregoing and X' represents —S— or —SO$_2$—.

That is, it can be obtained from a propiophenone (X) by forming a hydroxybutylophenone (XV) or a hydroxyacrylophenone (XVI) as an intermediate and then carrying out the substitution reaction.

Method E) (When X is —SO$_2$—)

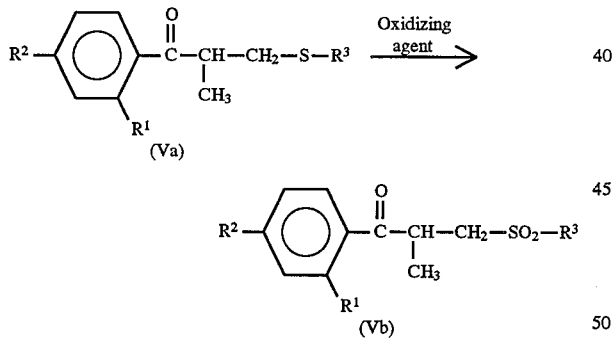

In this reaction formula, $R^1$, $R^2$, $R^3$ and X are as defined in the foregoing.

Thai is, it can be obtained by subjecting a compound in which X is S to oxidation with an appropriate oxidizing agent such as hydrogen peroxide, m-chloroperbenzoic acid or the like.

Next, typical examples of the compound represented by the formula (I) are shown in Table 1, though the present invention is not limited by these compounds. In the table, a diastereomer showing higher Rf value when measured by a silica gel TLC (a proper developing solvent was selected from ethyl acetate/n-hexane=1/0 to 1/1) was named A, and the other diastereomer showing lower Rf value was named B.

TABLE 1

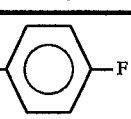

In the formula (I)
$R^2 = F$

| No | $R^1$ | $XR_3$ | Diastereomer A or B | Physical value or $^1$H-NMR(σ) |
|----|-------|--------|---------------------|-------------------------------|
| 1 | F | 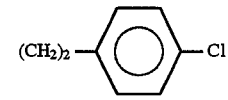 | diastereomer mixture A:B = 2:3 | diastereomer A: 8.0(s, 1H), 7.9(d, 2H), 7.3(m, 2H), 7.1(m, 1H), 6.9(m, 2H), 6.7 (m, 1H), 5.1(d, 1H), 4.5(d, 1H), 3.2(d, 1H), 2.3(q, 2H), 0.7(d, 3H) diastereomer B: 7.9(s, 1H), 7.8(s, 1 H), 7.3(m, 2H), 7.1(m, 1H), 6.6(m, 2H), 4.9(d, 1H), 4.5(d, 1H), 2.3(m, 3H), 1.1 (d, 3H) |
| 2 | F | 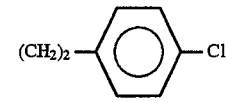 | diastereomer A | 7.8(s, 1H), 7.7(s, 1H), 7.4(m, 1H), 7.3 (d, 2H), 7.2(d, 2H), 6.7(m, 2H), 4.9(d, 1H), 4.5(d, 1H), 2.6(m, 2H), 2.1(m, 1 H), 1.8(m, 2H), 1.6(m, 1H), 1.4(m, 1H), 0.8(d, 3H) |
| 3 | F | 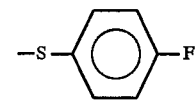 | diastereomer B | 7.7(s, 1H), 7.6(s, 1H), 7.3(m, 1H), 7.2 (d, 2H), 6.9(d, 2H), 6.6(m, 2H), 4.8(d, 1H), 4.4(d, 1H), 2.4(m, 2H), 2.0(m, 1 H), 1.6(m, 1H), 1.3(m, 1H), 1.1(m, 2H), 1.0(d, 3H) |
| 4 | H | 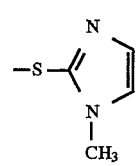 | diastereomer B | 7.8(s, 1H), 7.5(s, 1H), 7.1(m, 4H) 6.9 (m, 3H), 4.5(d, 1H), 4.4(d, 1H), 2.8(d, 1H), 2.5 (t, 1H), 2.0(m, 1H), 1.3(d, 3H) |
| 5 | H | 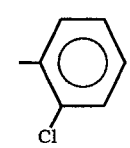 | diastereomer B | 7.9(s, 1H), 7.8(s, 1H), 7.2(m, 2H), 7.0 (s, 1H), 6.9(m, 2H), 6.9(s, 1H), 4.6(d, 1H), 4.5(d, 1H), 3.4(s, 3H), 3.2(d, 1 H), 2.3(m, 2H), 1.2(d, 3H) |
| 6 | F | 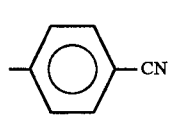 | diastereomer mixture A:B = 3:5 | diastereomer A: 7.9(s, 1H), 7.7(s, 1H), 7.5(m, 1H), 7.1–7.4(m, 2H), 6.8(m, 2 H), 4.9(dd, 1H), 4.9(dd, 1H), 4.6(dd, 1 H), 3.2(dd, 1H), 2.6(m, 2H), 0.6(dd, 3H) diastereomer B: 7.8(s, 1H), 7.7(s, 1 H), 7.5(d, 2H), 7.4(m, 2H), 7.1(d, 2H), 6.7(m, 2H), 4.9(d, 1H), 4.6(d, 1H), 2.5 (m, 3H), 1.3(d, 3H) |
| 7 | F | 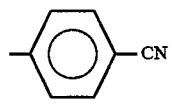 | diastereomer mixture A:B = 3:5 | diastereomer A: 8.1(s, 1H), 7.8(s, 1H), 7.6(d, 2H), 7.4(m, 1H), 7.3(d, 2H), 6.8 (m, 2H), 5.1(d, 1H), 4.6(d, 1H), 3.3(m, 1H), 2.5(m, 1H), 2.4(m, 1H), 0.6(d, 3H) diastereomer B: 8.0(s, 1H), 7.8(s, 1 H), 7.5(d, 2H), 7.4(m, 1H), 7.1(d, 2H), 6.8 (m, 2H), 4.9(d, 1H), 4.6(d, 1H), 2.6 (m, 1H), 2.4(d, 2H), 1.1(d, 3H) |
| 8 | F | 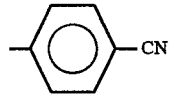 | diastereomer A | m.p. 145–146.5° C. |
| 9 | F | 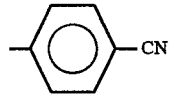 | diastereomer B | m.p. 155–155.5° C. |

TABLE 1-continued

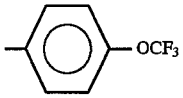

In the formula (I)
$R^2 = F$

| No | R¹ | XR₃ | Diastereomer A or B | Physical value or ¹H-NMR(σ) |
|---|---|---|---|---|
| 10 | F | 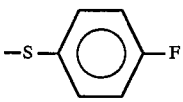 | diastereomer mixture A:B = 1:1 | diastereomer A: 7.9(s, 1H), 7.8(s, 1 H), 7.4(m, 1H), 7.1(d, 2H), 6.9(d, 2H), 6.7(m, 2H), 4.9(d, 1H), 4.6(d, 1H), 2.3 (m, 3H), 0.6(d, 3H) diastereomer B: 8.0(s, 1H), 7.8(s, 1H), 7.4(m, 1H), 7.3(d, 2H), 7.0(d, 2H), 6.8 (m, 2H), 5.0(d, 1H), 4.6(d, 1H), 3.2(d, 1H), 2.4(m, 2H), 1.1(d, 3H) |
| 11 | F |  | diastereomer mixture A:B = 2:3 | diastereomer A: 7.8(s, 1H), 7.7(s, 1H), 7.5(m, 2H), 7.1(m, 4H), 6.8(m, 2H), 4.6(d, 1H), 4.4(d, 1H), 3.4(d, 1H), 2.5(dd, 1H), 2.0(m, 1H), 1.0(d, 3H) diastereomer B: 7.8(s, 1H), 7.7(s, 1H), 7.4 (m, 2H), 7.0(m, 4H), 6.8(m, 2H), 4.5(d, 1 H), 4.4(d, 1H), 2.8(d, 1H), 2.5(dd, 1H), 2.0 (m, 1H), 1.3(d, 3H) |
| 12 | F | 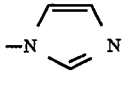 | diastereomer mixture A:B = 2:3 | diastereomer A: 7.9(s, 1H), 7.8(s, 1H), 7.5 (m, 1H), 7.3(m, 3H), 7.0(m, 2H), 6.8(m, 2 H), 5.0(d, 1H), 4.6(d, 1H), 3.2(d, 1H), 2.5 (m, 2H), 0.7(d, 3H) diastereomer B: 7.9(s, 1H), 7.8(s, 1H), 7.5(m, 1H), 7.3(m, 5H), 6.7(m, 2H), 4.9(d, 1H), 4.6(d, 1H), 2.4(m, 3H), 1.0(d, 3H) |
| 13 | H | 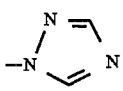 | diastereomer mixture A:B = 2:3 | diastereomer A: 7.9(s, 1H), 7.8(s, 1H), 7.4 (s, 1H), 7.3(m, 2H), 7.3(s, 1H), 6.9(m, 2 H), 6.8(s, 1H), 4.6(d, 1H), 4.4(d, 1H), 3.6 (d, 1H), 3.4(d, 1H), 2.3(m, 1H), 0.7(d, 3H) diastereomer B: 7.9(s, 1H), 7.8(s, 1H), 7.6 (s, 1H), 7.3(m, 2H), 7.2(s, 1H), 6.9(m, 2 H), 6.6(s, 1H), 4.5(d, 1H), 4.4(d, 1H), 3.7 (d, 1H), 3.4(d, 1H), 2.3(m, 1H), 1.1(d, 3H) |
| 14 | H | 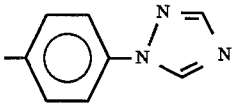 | diastereomer mixture A:B = 3:2 | diastereomer A: 8.1(s, 1H), 8.0(s, 1H), 7.8 (s, 1H), 7.7(s, 1H), 7.3(m, 2H) 6.9(m, 2 H), 4.6(d, 1H), 4.4(d, 1H), 3.9(m, 2H), 2.7 (m, 1H), 0.7(d, 3H) diastereomer B: 7.8(s, 1H), 7.7(s, 2H), 7.6(s, 1H), 7.3(m, 2H), 6.9(m, 2H), 4.7(d, 2H), 4.6(d, 1H), 2.8(m, 1H), 1.1(d, 3H) |
| 15 | F | 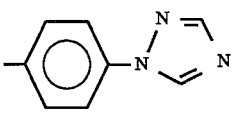 | diastereomer mixture A:B = 3:2 | diastereomer A: 8.6(s, 1H), 8.1(s, 1H), 7.9 (s, 1H), 7.8(s, 1H), 7.6(dd, 2H), 7.4(m, 1 H), 7.3(dd, 2H), 6.7(m, 2H), 5.0(d, 1H), 4.6 (d, 1H), 3.2(d, 1H), 2.4(m, 2H), 0.7(d, 3H) diastereomer B: 8.5(s, 1H), 8.1(s, 1H), 7.9(s, 1H), 7.8(s, 1H), 7.5(dd, 2H), 7.4(m, 1H), 7.1(dd, 2H), 6.7(m, 2H), 4.9(d, 1H), 4.6(d, 1 H), 2.4(m, 3H), 1.0(d, 3H) |
| 16 | F | 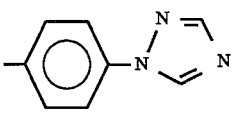 | diastereomer A | m.p. 75–77° C. |

TABLE 1-continued

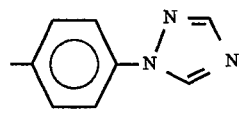

In the formula (I)
$R^2 = F$

| No | R¹ | XR₃ | Diastereomer A or B | Physical value or ¹H-NMR(σ) |
|---|---|---|---|---|
| 17 | F | 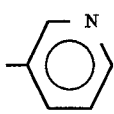 | diastereomer B | m.p. 138–139° C. |
| 18 | F | 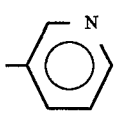 | diastereomer A | 8.5(s, 2H), 7.9(s, 1H), 7.8(s, 1H), 7.6(d, 1H), 7.5(m, 1H), 7.3(m, 1H), 6.7(m, 2H), 5.0(d, 1H), 4.6(d, 1H), 3.3(d, 1H), 2.9(d, 1H), 2.5(m, 1H), 0.7(d, 3H) |
| 19 | F | 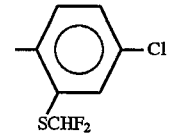 | diastereomer B | 8.4(d, 1H), 8.3(d, 1H), 7.8(d, 2H), 7.4(m, 1H), 7.3(m, 1H), 7.2(m, 1H), 6.8(m, 2H), 4.9(d, 1H), 4.6(d, 1H), 2.4(m, 3H), 1.1(d, 3H) |
| 20 | F | 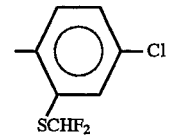 | diastereomer A | m.p. 106–110° C. |
| 21 | F | 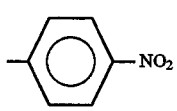 | diastereomer B | m.p. 134–137° C. |
| 22 | F | 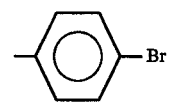 | diastereomer A | m.p. 140–143° C. |
| 23 | F | 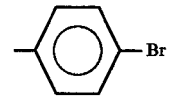 | diastereomer A | 7.8(s, 1H), 7.7(s, 1H), 7.5(m, 1H), 7.2(d, 2H), 7.0(d, 2H), 6.8(m, 2H), 5.0(d, 1H), 4.8(s, 1H), 4.6(d, 1H), 3.2(m, 1H), 2.4(m, 2H), 0.7(d, 3H) |
| 24 | F | 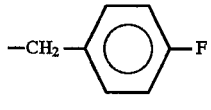 | diastereomer B | m.p. 133–136° C. |
| 25 | F | 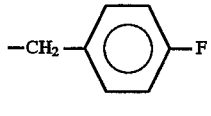 | diastereomer A | m.p. 102–103° C. |
| 26 | F | —CH₂—⟨C₆H₄⟩—F | diastereomer B | 7.7(s, 1H), 7.6(s, 1H), 7.3(m, 1H), 6.8(q, 4H), 6.6(m, 2H), 4.9(d, 1H), 4.6(s, 1H), 4.4(d, 1H), 2.7(m, 1H), 2.3(m, 1H), 1.6(m, 1H), 1.5(m, 2H), 1.2(d, 3H) |

TABLE 1-continued

In the formula (I)
$R^2 = F$

Structure: 4-F-phenyl(with $R^1$ at ortho)-C(OH)(CH$_2$-triazolyl)-CH(CH$_3$)-CH$_2$-X-R$^3$

| No | R¹ | XR₃ | Diastereomer A or B | Physical value or ¹H-NMR(σ) |
|---|---|---|---|---|
| 27 | F | -C₆H₄-CH=N-NH-CHO (para) | diastereomer mixture A:B = 1:1 | diastereomer A: 10.1(m, 1H), 8.8(m, 1H), 7.9(s, 1H), 7.8(s, 1H), 7.8(s, 1H), 7.6(m, 2H), 7.5(m, 1H), 7.0(m, 2H), 6.9(m, 2H), 5.1(d, 1H), 5.0(s, 1H), 4.7(d, 1H), 3.3(m, 1H), 2.4(m, 2H), 0.7(s, 3H) diastereomer B: 10.1(m, 1H), 8.7(m, 1H), 7.9(s, 1H), 7.8(s, 1H), 7.7(s, 1H) 7.6(m, 2H), 7.5(m, 1H), 6.9(m, 2H), 6.7(m, 2H), 5.1(d, 1H), 4.9(s, 1H), 4.8(d, 1H), 2.4(m, 3H), 1.1(d, 3H) |
| 28 | F | 3,4-dichlorophenyl | diastereomer A | 8.0(s, 1H), 7.8(s, 1H), 7.4(m, 2H), 7.2(m, 2H), 6.7(m, 2H), 5.0(d, 2H), 4.9(s, 1H), 4.8(d, 1H), 3.3(q, 1H), 2.5(m, 2H), 0.6(d, 3H) |
| 29 | F | 3,4-dichlorophenyl | diastereomer B | m.p. 125–130° C. |
| 30 | F | 4-SO₂CH₃-phenyl | diastereomer mixture A:B = 2:3 | diastereomer A: 7.9(s, 1H), 7.8(s, 1H), 7.8 (d, 2H), 7.4(m, 1H), 7.2(d, 2H), 6.7(m, 2H), 5.1(d, 1H), 4.9(s, 1H), 3.3(m, 1H), 2.5 (m, 2H), 0.6(d, 3H) diastereomer B: 7.9(s, 1H), 7.8(s, 1H), 7.8(d, 2H), 7.4(d, 2H), 7.4(d, 2H), 6.8(m, 2H), 4.8(d, 2H), 4.8(s, 1H), 4.6(d, 1H), 2.5(m, 3H), 1.1(d, 3H) |
| 31 | F | 4-(3-methyl-5-oxo-4,5-dihydro-1,2,4-triazol-4-yl)phenyl | diastereomer mixture A:B = 5:4 | diastereomer A: 7.9(s, 1H), 7.8(s, 1H), 7.7 (s, 1H), 7.6(d, 2H), 7.5(m, 1H), 7.4(d, 2H), 6.7(m, 2H), 5.1(d, 1H), 5.0(s, 1H), 4.6 (d, 1H), 3.6(s, 3H), 3.3(m, 1H), 2.5(m, 2H), 0.7(d, 3H) diastereomer B: 7.8(s, 1H), 7.6(s, 1H), 7.5(s, 1H), 7.4(d, 2H), 7.3(m, 1H), 7.2(d, 2H), 6.7(m, 2H), 4.9(d, 2H), 4.8( s, 1H), 4.6(d, 1H), 3.5(s, 3H), 2.5(m, 3H), 1.1(d, 3H) |
| 32 | F | 3,4-difluorophenyl | diastereomer A | m.p. 78–82° C. |
| 33 | F | 3,4-difluorophenyl | diastereomer B | 7.8(s, 1H), 7.7(s, 1H), 7.4(m, H), 6.9(m, 1H), 6.7(m, 4H), 4.9(d, 1H), 4.8(s, 1H), 4.6(d, 1H), 2.4(m, 3H), 1.1(d, 3H) |

TABLE 1-continued

In the formula (I) $R^2 = F$

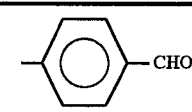

| No | R¹ | XR₃ | Diastereomer A or B | Physical value or ¹H-NMR(σ) |
|---|---|---|---|---|
| 34 | F | 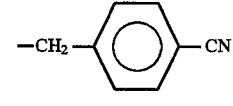—CHO | diastereomer mixture A:B = 4:3 | diastereomer A: 9.9(s, 1H), 7.9(s, 1H), 7.8 (s, 1H), 7.5(m, 1H), 7.4(m, 2H), 7.2(m, 1H), 6.7(m, 2H), 5.0(d, 1H), 4.9(s, 1H), 4.7 (d, 1H), 3.3(m, 1H), 2.4(m, 2H), 0.7(d, 3H) diastereomer B: 9.9(s, 1H), 7.9(s, 1H), 7.7(s, 1H), 7.5(m, 1H), 7.4(m, 2H), 7.2 (m, 2H), 6.8(m, 2H), 4.9(d, 1H), 4.8(s, 1H), 4.7(d,1H), 2.3(m, 3H), 1.1(d, 3H) |
| 35 | F | —CH₂—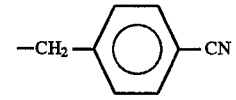—CN | diastereomer A | m.p. 112–113° C. |
| 36 | F | —CH₂—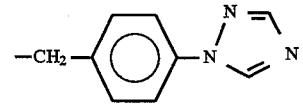—CN | diastereomer B | m.p. 95–97° C. |
| 37 | F | —CH₂—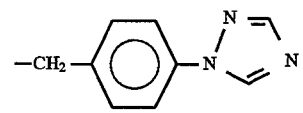 | diastereomer A | 8.5(s, 1H), 8.1(s, 1H), 7.8(s, 1H), 7.7(s, 1H), 7.6(d, 2H), 7.4(m, 1H), 7.4(d, 2H), 6.7(m, 1H), 5.0(d, 1H), 4.8(s, 1H), 4.5(d, 1H), 2.8(m, 1H), 2.6(m, 1H), 2.1(m, 3H), 0.9(d, 3H) |
| 38 | F | —CH₂—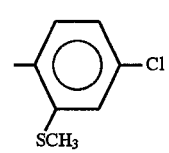 | diastereomer B | 8.5(s, 1H), 8.0(s, 1H), 7.8(s, 1H), 7.7(s, 1H), 7.5(d, 2H), 7.4(m, 1H), 7.1(d, 2H), 6.7(m, 2H), 4.9(d, 1H), 4.6(s, 1H), 4.5(d, 1H), 4.1(m, 1H), 2.8(m, 1H), 2.6(m, 1H), 1.3(m, 2H), 1.2(d, 3H) |
| 39 | F | 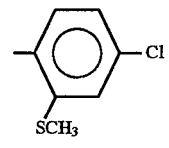 | diastereomer A | m.p. 95–98° C. |
| 40 | F | 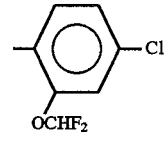 | diastereomer B | m.p. 108–112° C. |
| 41 | F | 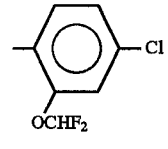 | diastereomer A | 7.8(s, 1H), 7.7(s, 1H), 7.5(m, 1H), 7.1(m, 3H), 6.7(m, 2H), 6.4(t, 1H), 5.0(d, 1H), 4.8(s, 1H), 4.7(d, 1H), 3.2(d, 1H), 2.5(m, 2H), 0.6(d, 3H) |
| 42 | F | (same as 41) | diastereomer B | m.p. 154–156° C. |

TABLE 1-continued

In the formula (I)
$R^2 = F$

| No | $R^1$ | $XR_3$ | Diastereomer A or B | Physical value or $^1$H-NMR(σ) |
|---|---|---|---|---|
| 43 | F | ![4-CF3-phenyl] -⟨phenyl⟩-CF$_3$ | diastereomer mixture A:B = 3:4 | diastereomer A: 7.8(s, 1H), 7.7(s, 1H), 7.6 (m, 2H), 7.5(m, 1H), 7.3(m, 2H), 6.7(m, 2H), 5.0(d, 1H), 4.9(s, 1H), 4.6(d, 1H), 4.3 (m, 1H), 3.4(m, 2H), 0.6(d, 3H) diastereomer B: 7.8(s, 1H), 7.7(s, 1H), 7.5(m, 2H), 7.4(m, 1H), 7.0(m, 2H), 6.7(m, 2H), 4.9(d, 1H), 4.8(s, 1H), 4.7(d, 1H), 2.4(m, 3H), 1.1(d, 3H) |

Of the compounds listed above, the following are preferred, that is to say Compound Nos. 1, 2, 6, 7, 8, 9, 10, 11, 12, 15, 18, 20, 21, 23, 26, 28, 30, 33, 35, 37, 38, 39 and 41. The more preferred compounds are Compound Nos. 1, 2, 7, 8, 10, 11, 15, 18, 20, 23, 26, 28, 37, 39 and 41. The most preferred compounds are Compound Nos. 8, 20 and 28.

The compound of the present invention is an antifungal agent useful for the treatment of fungal infection in human and animals. For example, it can be used for the treatment of local fungal infection, mucosal infection and systemic fungal infection caused by fungi belonging to the genera Trichophyton, Candida, Aspergillus and the like. The compound of the present invention is used alone or as a composition consisting of the compound and a pharmaceutically acceptable carrier or diluent, by making the compound or composition into suitable dosage forms for oral or parenteral administration, such as solutions, tablets, suppositories, emulsions, ointments, creams, lotions, cataplasmas and the like.

Its dose varies depending for example on the symptoms of each disease, age and weight of each patient and the form of administration. In the case of systemic-treatment, it may be administered in a dose of from 0.05 to 100.mg, preferably from 0.5 to 50 mg, per 1 kg weight per adult per day, by dividing the daily dose into one to several doses per day.

Concentration of the active ingredient for topical treatment may be in the range of from 0.001 to 5%, preferably from 0.1 to 2%.

As a matter of course, the agent of the present invention may be used by mixing it with other antifungal or antibacterial agents such as trichomycin, valitoin, clotrimazole and the like.

The following examples are provided to further illustrate the present invention. It is to be understood, however, that the examples are for purpose of illustration only and are not intended as a definition of the limits of the invention.

EXAMPLE 1

Synthesis of 2-(2,4-difluorophenyl)-2-[1-methyl-2-(4-fluorophenyl)-ethyl]-1-triazolyl-2-ethanol (compound No. 11)

1) A 4 g portion of 2,4-difluoropropiophenone and 3.5 g of p-fluorobenzaldehyde were dissolved in 40 ml of methanol, and the solution was mixed with 0.2 g of sodium hydroxide at room temperature and stirred overnight at the same temperature. After removing methanol by evaporation under a reduced pressure, the resulting residue was poured into water and extracted with ethyl acetate. The resulting organic layer was washed with water and dried on anhydrous magnesium sulfate, subsequently removing the solvent by evaporation under a reduced pressure. The resulting residue was then purified by a silica gel column chromatography (ethyl acetate:n-hexane=1:5) to obtain 3.0 g of 2',4'-difluorophenyl-1-methyl-3-(4-fluorophenyl)-acrylophenone with a yield of 45%.

2) A 7.4 g portion of trimethylsulfonium iodide was dissolved in 30 ml of dimethyl sulfoxide and cooled to 15° C. To the resulting solution was added 4.1 g of potassium t-butoxide at 15° C. or below, followed by 1 hour of stirring at the same temperature. At a temperature of 15° C. or below, to this was added dropwise 10 ml of dimethyl sulfoxide solution containing 2.0 g of 2',4'-difluorophenyl-1-methyl-3-(4-fluorophenyl)-acrylophenone. After stirring overnight at room temperature, the reaction solution was poured into ice water and extracted with ethyl acetate, the resulting organic layer was washed with water and dried on anhydrous magnesium sulfate, and then the solvent was removed by evaporation under a reduced pressure to obtain 2.0 g of 2-(2,4-difluorophenyl)-2-[1-methyl-2-(4-fluorophenyl)-ethenyl]-oxirane with a yield of 96%.

3) To 40 ml of N,N-dimethylformamide Were dissolved 2.0 g of 2-(2,4-difluorophenyl)-2-[1-methyl-2-(4-fluorophenyl)-ethenyl]-oxirane, 1.9 g of 1,2,4-triazole and 1.6 g of potassium t-butoxide. After 4 hours of stirring at 100° C., the reaction solution was cooled to room temperature, poured into ice water and then extracted with ethyl acetate. The resulting organic layer was washed with water and dried on anhydrous magnesium sulfate. After removing the solvent by evaporation under a reduced pressure, the resulting residue was purified by a silica gel column chromatography (ethyl acetate) to obtain 1.6 g of 2-(2,4-difluorophenyl)-2-[1-methyl-2-(4-fluorophenyl)-ethenyl]-1-triazolyl-2-ethanol with a yield of 36%.

4) A 0.3 g portion of 2-(2,4-difluorophenyl)-2-[1-methyl-2-(4-fluorophenyl)-ethenyl]-1-triazolyl-2-ethanol was dissolved in 20 ml of acetic acid and subjected to 4 hours of hydrogenation under normal pressure in the presence of 0.02 g 10% Pd-carbon. After completion of the reaction, acetic acid was removed by evaporation under a reduced pressure, and the thus obtained residue was poured into water, neutralized with sodium bicarbonate and then extracted with ethyl acetate. The resulting organic layer was washed with water and dried on anhydrous magnesium sulfate. After removing the solvent by evaporation under a reduced pressure, the resulting residue was purified by a silica gel column chromatography to obtain 0.15 g of 2-(2,4-difluorophenyl)-1-triazolyl-3-methyl-4-(4-fluorophenyl)-2-butanol with a yield of 48%.

EXAMPLE 2

Synthesis of 1-triazolyl-2-(4-fluorophenyl)-3-methyl-4-(4-fluorophenyl)-mercapto-2-butanol (compound No. 4)

1) A 0.5 g portion of p-fluoro-3-hydroxyacrylophenone and 0.3 g of triethylamine were dissolved in 30 ml of methylene chloride to which was subsequently added dropwise 0.35 g of methanesulfonic acid chloride while cooling in an ice bath. After 3 hours of stirring at room temperature, the reaction solution was washed with water, the organic layer was dried on anhydrous magnesium sulfate and then the solvent was removed by evaporation under a reduced pressure to obtain 0.6 g of 1'-(4-fluorophenyl)-2'-methyl-1'-oxo-2'-propenyl methanesulfonic acid ester with a yield of 83%.

2) To 0.3 g of fluorothiophenol dissolved in 20 ml of acetone were added 0.35 g of potassium carbonate and, with cooling in an ice bath, 0.6 g of 1'-(4-fluorophenyl)-2'-methyl-1'-oxo-2'-propenyl methanesulfonic acid ester. After 4 hours of stirring at room temperature, the reaction solution was poured into ice water and extracted with ethyl acetate. The thus obtained organic layer was washed with water and dried on anhydrous magnesium sulfate, the solvent was removed by evaporation under a reduced pressure and then the resulting residue was purified by a silica gel column chromatography (ethyl acetate:n-hexane=1:5) to obtain 0.8 g of 4-fluoro-3-(4-fluorophenyl)-mercaptoacrylophenone with a yield of 100%.

3) A 2.8 g portion of trimethylsulfonium iodide was dissolved in 50 ml of dimethyl sulfoxide and cooled to 15° C. To the thus prepared solution was added 1.6 g of potassium t-butoxide at a temperature of 15° C. or below, followed by 1 hour of stirring at the same temperature. At a temperature of 15° C. or below, to this was added dropwise 0.8 g of 4-fluoro-3-(4-fluorophenyl)-mercaptoacrylophenone which has been dissolved in 5 ml of dimethyl sulfoxide. After stirring overnight at room temperature, the reaction solution was poured into ice water and extracted with ethyl acetate, the resulting organic layer was washed with water and dried on anhydrous magnesium sulfate and then the solvent was removed by evaporation under a reduced pressure to obtain 0.8 g of 2-(4-fluorophenyl)-3-methyl-4-(4-fluorophenyl)-mercapto-1,2-epoxy-3-butene with a yield of 95%.

4) A 0.8 g portion of 2-(4-fluorophenyl)-3-methyl-4-(4-fluorophenyl)-mercapto-1,2-epoxy-3-butene and 0.6 g of potassium t-butoxide were dissolved in 30 ml of N,N-dimethylformamide and stirred at 100° C. for 4 hours. After cooling to room temperature, the reaction solution was poured into ice water and extracted with ethyl acetate, and the resulting organic layer was washed with water and dried on anhydrous magnesium sulfate. After removing the solvent by evaporation under a reduced pressure, the resulting residue was purified by a silica gel column chromatography (ethyl acetate:n-hexane=1:1) to obtain 0.4 g of 1-triazolyl-2-(4-fluorophenyl)-3-methyl-4-(4-fluorophenyl)-mercapto-3-buten-2-ol with a yield of 39%.

5) A 0.08 g portion of lithium aluminium hydride was added to 10 ml of tetrahydrofuran. Spending 20 minutes or more, to this was added dropwise 0.2 g of 1-triazolyl-2-(4-fluorophenyl)-3-methyl-4-(4-fluorophenyl)-mercapto-3-buten-2-ol which has been dissolved in 3 ml of tetrahydrofuran. After 5 hours or more of stirring at room temperature, after-treatment was carried out in the usual way, and the product was purified by a silica gel column chromatography (ethyl acetate:n-hexane=2:1) to obtain 0.15 g of 1-triazotyl-2-(4-fluorophenyl)-3-methyl-4-(4-fluorophenyl)-mercapto-2-butanol with a yield of 75%.

EXAMPLE 3

Synthesis of 1-triazolyl-2-(2,4-difluorophenyl)-3-methyl-4-(4-cyanophenyl)-2-butanol (compound Nos. 7, 8 and 9)

1) A 19 g portion of 2,4-difluoropropiophenone was dissolved in 150 ml of tetrahydrofuran. With cooling in a dry ice-acetone bath and spending 20 minutes or more, to this was added dropwise 112 ml of 1N tetrahydrofuran solution of lithium hexamethyl disilazide. After 1 hour of stirring at the same temperature, to this was further added dropwise 50 ml of tetrahydrofuran solution containing 14 g of 4-cyanobenzyl bromide spending 20 minutes or more, followed by overnight stirring at room temperature. The reaction solution was mixed with saturated ammonium chloride aqueous solution, poured into water and then extracted with ethyl acetate. The thus obtained organic layer was washed with water and dried on anhydrous magnesium sulfate. After removing the solvent by evaporation under a reduced pressure, the resulting residue was purified by a silica gel column chromatography (ethyl acetate:n-hexane=1:9) to obtain 13 g of 2',4'-difluoro-2-methyl-3-(4-cyanophenyl)-propiophenone with a yield of 41%.

2) A 1.0 g portion of 60% sodium hydride was dissolved in 50 ml of dimethyl sulfoxide and stirred at 60° C. for 1 hour. This was cooled to 15° C. and mixed with 5.6 g of trimethylsulfoxonium iodide. The reaction mixture was stirred at room temperature for 1 hour, cooled again to 15° C. and then mixed with 10 ml of dimethyl sulfoxide solution containing 2.4 g of 2,4-difluoro-2-methyl-3-(4-cyanophenyl)-propiophenone. After 1 hour of stirring at 60° C., the reaction solution was cooled to room temperature, poured into ice water and then extracted with ethyl acetate. The thus obtained organic layer was washed with water and dried on anhydrous magnesium sulfate and then the solvent was removed by evaporation under a reduced pressure to obtain 2.3 g of 2-(2,4-difluorophenyl)-3-methyl-4-(4-cyanophenyl)-1,2-butane oxide with a yield of 95%.

3) A 2.3 g portion of 2-(2,4-difluorophenyl)-3-methyl-4-(4-cyanophenyl)-1,2-butane oxide was dissolved in 50 ml of N,N-dimethylformamide, and the solution was mixed with 2.1 g of 1,2,4-triazole and 2.0 g of t-butoxypotassium and stirred at 100° C. for 2 hours. The reaction solution was cooled to room temperature, poured into ice water and then extracted with ethyl acetate. The thus obtained organic layer was washed with water and dried on anhydrous magnesium sulfate, the solvent was removed by evaporation under a reduced pressure and then the resulting residue was purified by a silica gel column chromatography (ethyl acetate:n-hexane=2:1) to obtain 1.5 g of 1-triazolyl-2-(2,4-difluorophenyl)-3-methyl-4-(4-cyanophenyl)-2-butanol with a yield of 52%.

4) A 1.2 g portion of 1-triazolyl-2-(2,4-difluorophenyl)-3-methyl-4-(4-cyanophenyl)-2-butanol was dissolved in a solvent and separated by a high performance liquid chromatography using a preparative column (μ-bonder sphere 19 mm×15 cm). In this manner, 0.5 g of erythro form having a quick retention time and 0.4 g of threo form having a slow retention time were obtained.

EXAMPLE 4

Synthesis of 2-(2,4-difluorophenyl)-3-methyl-5-(4-triazolphenyl)-1-triazolyl-pentan-2-ol (compoond Nos. 37 and 38)

1) A 42 g portion of α-methyl-2,4-difluorophenyl bromide dissolved in 80 ml of ethanol was added with 3.3 g of $NaBH_4$ and stirred at room temperature for 2 hours. The reaction solution was poured into ice water and extracted with ethyl acetate. After washing and drying, the solvent was removed by evaporation under a reduced pressure to obtain 38 g of 1-(2,4-difluorophenyl)-2-bromopropanol with a yield of 88%.

2) A 25 g portion of 1-(2,4-difluorophenyl)-2-bromopropanol was dissolved in 80 ml of dimethyl sulfoxide to which was subsequently added 100 ml of 25% KOH aqueous solution at 20° C. or below. After 1 hour of stirring at 20° C., the reaction solution was poured into ice water and extracted with ethyl acetate. After washing and drying, the solvent was removed by evaporation under a reduced pressure to obtain 14 g of 2-(2,4-difluorophenyl)-2-propylene-1-oxide with a yield of 81%.

3) A 17 g portion of lithium acetylide ethylenediamine and 14 g of 2-(2,4-difluorophenyl)-2-propylene oxide were stirred at room temperature for 2 days in a mixture solvent consisting of 40 ml dimethyl sulfoxide and 45 ml hexamethylphosphoramide. The reaction solution was poured into ice water and extracted with ethyl acetate. After washing and drying, the solvent was removed by evaporation under a reduced pressure, and the thus concentrated residue was purified by a silica gel column chromatography (ethyl acetate:n-hexane=1:4) to obtain 9 g of 1(2,4-difluorophenyl)-2-acetylenyl-1-propanol with a yield of 60%.

4) A 7 g portion of 4-fluoronitrobenzene, 7 g of 1,2,4-triazole and 7.6 g of potassium carbonate were dissolved in 40 ml of N-methylpyrrolidone and stirred at 100° C. for 4 hours. After cooling to room temperature, the reaction solution was poured into water and extracted with ethyl acetate. After washing with 1N hydrochloric acid and water in that order and subsequent drying, the solvent was removed by evaporation under a reduced pressure to obtain 8 g of 4-triazolylnitrobenzene with a yield of 85%.

5) A 5 g portion of 4-triazolylnitrobenzene dissolved in 20 ml of acetic acid was mixed with 0.3 g of 10% Pd-carbon and subjected to hydrogenation under a hydrogen pressure of 3 $kg/cm^2$. The reaction solution was poured into water and extracted with chloroform. The resulting organic layer was washed with sodium bicarbonate aqueous solution and water in that order and dried, and the solvent was removed by evaporation under a reduced pressure to obtain 3 g of 4-triazolylaniline with a yield of 71%.

6) A 3 g portion of 4-triazolylaniline was added to 50 ml of 2.4N hydrochloric acid to which was subsequently added dropwise 6 ml of aqueous solution containing 5 g of $NaNO_2$ at a temperature of 5° C. or below. After 15 minutes of stirring at the same temperature, this was poured into 40 ml of water containing 11 g of KI and stirred overnight at room temperature. After removing insoluble matter by filtration, the resulting filtrate was extracted with dimethyl ether. The thus obtained organic layer was washed with NaOH aqueous solution and water in that order and dried, the solvent was removed by evaporation under a reduced pressure and then the resulting residue was purified by a silica gel column chromatography (ethyl acetate:n-hexane=2:1) to obtain 2.25 g of 4-triazolyliodobenzene with a yield of 45%.

7) To 10 ml of triethylamine were added 0.3 g of 1-(2,4-difluorophenyl)-2-acetylenyl-1-propanol, 35 mg of dichlorobistriphenylphosphinyl palladium, 0.45 g of 4-triazolyliodobenzene and 20 mg of copper iodide. After 24 hours of stirring at room temperature, the reaction solution was poured into water and extracted with ethyl acetate, the resulting extract was washed with water and dried, the solvent was removed by evaporation under a reduced pressure and then the resulting residue was purified by a Silica gel column chromatography (ethyl acetate) to obtain 0.4 g of 1-(2,4-difluorophenyl)-4-(4-triazolphenyl)-2-methyl-3-butyne-1-ol with a yield of 71%.

8) A 1.3 g portion of 1-(2,4-difluorophenyl)-4-(4-triazolphenyl)-2-methyl-3-butyne-1-ol and 0.2 g of 10% Pd-carbon were added to 15 ml of methanol and subjected to hydrogenation under a hydrogen pressure of 1 $kg/cm^2$. After removing insoluble matter by filtration,-the resulting filtrate was poured into water and extracted with ethyl acetate. After washing and drying, the solvent was removed by evaporation under a reduced pressure to obtain 1.3 g of 1-(2,4-difluorophenyl)-4-(4-triazolphenyl)-2-methyl-3-butyl alcohol with a yield of 99%.

9) A 1.3 g portion of 1-(2,4-difluorophenyl)-4-(4-triazolphenyl)-2-methyl-3-butyl alcohol dissolved in 20 ml of methylene chloride was mixed with 1.3 g of pyridinium chlorochromate and stirred at room temperature for 2 hours. After removing insoluble matter by filtration, the filtrate was concentrated under a reduced pressure, and the resulting residue was purified by a silica gel column chromatography (ethyl acetate:n-hexane=1:2) to obtain 0.6 g of 1-(2,4-difluorophenyl)-4-(4-triazolphenyl)-2-methyl-3-butane-1-one with a yield of 46%.

10) A 0.9 g portion of trimethylsulfonium iodide was dissolved in 4 ml of dimethyl sulfoxide and cooled to 15° C. This was mixed with 0.5 g of t-butoxy potassium at a temperature of 15° C. or below, and the mixture was stirred for 1 hour at the same temperature. To this was added dropwise 1 ml of dimethyl sulfoxide solution containing 0.3 g of 1-(2,4-difluorophenyl)-4-(4-triazolphenyl)-2-methyl-3-butane-1-one at a temperature of 15° C. or below. After 1 hour of stirring at room temperature, the reaction solution was poured into ice water and extracted with ethyl acetate to obtain 0.3 g of 2-(2,4-difluorophenyl)-2-[1-methyl-3-(4-triazolphnyl)-propyl]-oxirane with a yield of 96%.

11) A 0.3 g portion of 2-(2,4-difluorophenyl)-2-[1-methyl-3-(4-triazolphenyl)-propyl]-oxirane, 0.24 g of 1,2,4-triazole and 0.2 g of potassium t-butoxide were added to 5 ml of dimethylformamide and stirred at 100° C. for 5 hours. After cooling to room temperature, the reaction solution was poured into ice water and extracted with ethyl acetate. The resulting organic layer was washed with water and dried on anhydrous magnesium sulfate, the solvent was removed by evaporation under a reduced pressure and then the resulting residue was purified by a silica gel column chromatography (ethyl acetate) to obtain 70 mg of a compound having a large Rf value (compound No. 37) and 40 mg of another compound having a small Rf value (compound No. 38).

Next, formulation examples are shown below by way of illustration and not byway of limitation. In the following, the term "part(s)" means "weight part(s)".

FORMULATION EXAMPLE 1

| | |
|---|---|
| inventive compound | 0.01 part |
| 0.5% carboxymethylcellulose | 99.9 parts |

The former was suspended in the latter to obtain a suspension preparation.

FORMULATION EXAMPLE 2

| | |
|---|---|
| inventive compound | 1 part |
| polyethylene glycol 400 | 99 parts |

These ingredients were mixed and solubilized to obtain a solution preparation for application use.

FORMULATION EXAMPLE 3

| | |
|---|---|
| inventive compound | 2 parts |
| polyethylene glycol 400 | 49 parts |
| polyethylene glycol 4000 | 49 parts |

These ingredients were mixed and solubilized under heating and then cooled to obtain an ointment preparation.

FORMULATION EXAMPLE 4

| | |
|---|---|
| inventive compound | 3 parts |
| 1,2-propanediol | 5 parts |
| glycerol stearate | 5 parts |
| spermaceti | 5 parts |
| isopropyl myristate | 10 parts |
| polysorbate | 4 parts |

These ingredients were mixed, heated, cooled and then stirred by adding 68 parts of water to obtain a cream preparation.

FORMULATION EXAMPLE 5

| | |
|---|---|
| inventive compound | 0.1 part |
| stearyl alcohol | 5.0 parts |
| cetanol | 5.0 parts |
| middle chain fatty acid triglyceride | 10.0 parts |
| isopropyl myristate | 5.0 parts |
| polysorbate 60 | 4.0 parts |
| sorbitan monostearate | 1.0 part |
| methyl paraoxybenzoate | 0.14 part |
| propyl paraoxybenzoate | 0.06 part |
| dibutylhydroxytoluene | 0.02 part |
| purified water | balance |

These ingredients were made into a cream preparation in the usual way.

TEST EXAMPLE 1

A 0.1 ml portion of a cell suspension of *Candida albicans* IFO 1270 ($1.0 \times 10^7$ cells/ml) and a 0.1 ml portion of each test compound dissolved in dimethylsulfoxide were added to 9.8 ml of Sabouraudp's glucose broth.

Final compound concentrations in the culture were 10 µg/ml or 0.1 µg/ml. After incubation On a reciprocal shaker at 37° C. for 48 hrs, growth inhibition ratio of each test compound was measured. The results are shown in Table 2.

TABLE 2

| | Growth inhibition ratio (%) | |
|---|---|---|
| Compound No. | 10 µg/ml | 0.1 µg/ml |
| 1 | 85 | 71 |
| 2 | 76 | 60 |
| 3 | 74 | 58 |
| 4 | 72 | 6 |
| 5 | 10 | 5 |
| 7 | 74 | 53 |
| 8 | 78 | 59 |
| 11 | 74 | 45 |
| 14 | 20 | 2 |
| 15 | 66 | 53 |
| 20 | 68 | 53 |
| 22 | 70 | 58 |
| 25 | 70 | 60 |
| 30 | 63 | 6 |
| 35 | 74 | 60 |
| 39 | 68 | 53 |
| control drug A | 77 | 59 |

Control drug A: cis-1-acetyl-4-[4-[[2-(2,4-dichlorophenyl)-2-(imidazol-1-ylmethyl)-1,3-dioxolan-4-yl]methoxy]phenyl]piperazine (general name: ketoconazole)

TEST EXAMPLE 2

Male ddy mice at six weeks of age were divided into a control group of 10 animals and drug administration groups of 5 animals each.

Subculture was carried out at 37° C. for 24 hrs Sabouraudp's glucose agar (manufactured by Difco laboratory).

A cell suspension of *C. albicans* IFO 1270 ($2.5 \times 10^7$ cells/ml) was intravenously inoculated in an amount of 4 ml/kg, and each test compound was orally administered in a dose of 10 mg/kg once a day for 3 consecutive days. Examination of survival ratio was carried out 10 days after the inoculation of fungi. The results are shown in Table 3.

TABLE 3

| Compound No. | Survival ratio (%) |
|---|---|
| 1 | 80 |
| 2 | 80 |
| 3 | 60 |
| 4 | 0 |
| 5 | 0 |
| 7 | 100 |
| 8 | 100 |
| 10 | 100 |
| 11 | 60 |
| 14 | 20 |
| 15 | 100 |
| 16 | 100 |
| 17 | 60 |
| 18 | 40 |
| 20 | 100 |
| 22 | 100 |
| 27 | 40 |
| 28 | 100 |
| 30 | 100 |
| 31 | 80 |
| 32 | 80 |
| 37 | 80 |

TABLE 3-continued

| Compound No. | Survival ratio (%) |
| --- | --- |
| 39 | 100 |
| 43 | 100 |
| Control drug A | 20 |

Thus, it is apparent that the triazole derivative of the present invention are antifungal agents which are expected to be useful for the treatment of fungal infection in human and animals.

While the invention has been described in detail and with reference to specific examples thereof, it will be apparent to one skilled in the art that various changes and modifications can be made therein without departing from the spirit and scope thereof.

What is claimed is:

1. A triazole compound or a pharmacologically acceptable salt thereof represented by the following formula (I)

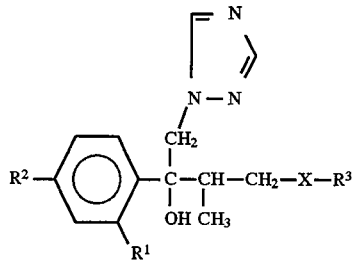

(I)

wherein $R^1$ and $R^2$ are the same or different from each other and each represents a hydrogen atom, a halogen atom, or a $C_1$–$C_6$ trihaloalkyl group, $R^3$ represents a phenyl group substituted with 1 to 2 substituting groups selected from the group consisting of a cyano group, a nitro group,

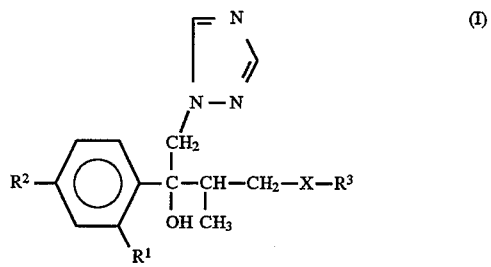

and X represents —$(CH_2)_n$— where n is 0 or an integer of 1 to 2.

2. An antifungal composition which contains, as its active ingredient, a triazole compound or a pharmacologically acceptable salt thereof represented by the following formula (I)

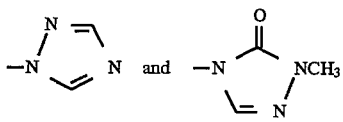

(I)

wherein $R^1$ and $R^2$ are the same or different from each other and each represents a hydrogen atom, a halogen atom, or a $C_1$–$C_6$ trihaloalkyl group, $R^3$ represents a phenyl group substituted with 1 to 2 substituting groups selected from the group consisting of a cyano group, a nitro group,

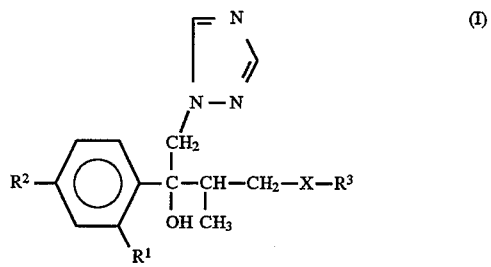

and X represents —$(CH_2)_n$— where n is 0 or an integer of 1 to 2 and a pharmaceutically acceptable carrier or diluent.

3. A method for treating fungal infection which comprises administering to human or animals an effective amount of a triazole compound or a pharmacologically acceptable salt thereof as claimed in claim 1.

* * * * *